United States Patent [19]

Patel et al.

[11] Patent Number: 5,478,734
[45] Date of Patent: Dec. 26, 1995

[54] METHOD OF CHIRAL EPOXIDATION OF BENZOPYRAN OR PYRANOPYRIDINE DERIVATIVES USING MICROORGANISMS

[75] Inventors: Ramesh N. Patel, Bridgewater, N.J.; Amit Banerjee, Yardley, Pa.; Clyde McNamee, Lawrenceville, N.J.; David Brzozowski, South Plainfield, N.J.; Laszlo J. Szarka, East Brunswick, N.J.

[73] Assignee: Bristol-Myers Squibb Company, Princeton, N.J.

[21] Appl. No.: 192,918

[22] Filed: Feb. 7, 1994

Related U.S. Application Data

[63] Continuation-in-part of Ser. No. 79,712, Jun. 18, 1993, abandoned.

[51] Int. Cl.$^6$ .............................. C12P 17/18; C12P 17/06
[52] U.S. Cl. ......................... 435/119; 435/125; 435/280
[58] Field of Search ................................. 435/119, 125, 435/280

[56] References Cited

U.S. PATENT DOCUMENTS

5,358,860  10/1994  Hager et al. ............................ 435/123

FOREIGN PATENT DOCUMENTS

WO93/04182  3/1993  WIPO .

OTHER PUBLICATIONS

H. A. J. Carless, "Enantiospecific and Stereoselective Synthesis of (−)-Conduritol C from Chlorobenzene via Microbial Oxidation and Epoxidation", *J. Chem. Soc. Chem. Commun.*, (1992), pp. 234–235.

K. Furuhashi, "A Fermentation Process for the Production of Optically Active Epoxides", *Chem. Econo. & Eng. Review*, Jul./Aug. (1986), 18:7–8 (No. 200), pp. 21–26.

P. J. van Bladeren et al., "Differential Stereoselectivity of Cytochromes P-450b and P-405c in the Formation of Naphthalene and Anthracene 1,2-Oxides", *The J. of Biological Chem.*, Aug. 25, (1985), 260:18, pp. 10226–10235.

T. Nakamura et al., "Resolution and Some Properties of Enzymes Involved in Enantioselective Transformation of 1,3-Dichloro-2-Propanol to (R)-3-Chloro-1,2-Propanediol by *Corynebacterium* sp. Strain N-1074", *J. of Bacteriology*, Dec. (1992), 174:23, pp. 7613–7619.

X. M. Zhang et al., "Microbiological Transformations, 19. Asymmetric Dihydroxylation of the Remote Double Bond of Geraniol: A Unique Stereochemical Control Allowing Easy Access to Both Enantiomers of Geraniol–6,7–diol", *J. Org. Chem.*, (1991), 56, pp. 3814–3817.

M. Mahmoudian et al., "Stereoselective epoxidation of phenyl allyl either by alkene–utilizing bacteria", *Appl. Microbiol Biotechnol*, (1992), 37, pp. 28–31.

M. Mahmoudian et al., "Biocatalysts for production of chiral epoxides", *Appl. Microbiol Biotechnol*, (1992), 37, pp. 23–27.

F. S. Sariaslani et al., "Microbial Transformation of Precocene II: Oxidative Reactions by Streptomyces griseus", *Appl. and Environ. Microbiology*, (1987), 53:8, pp. 1780–1784.

D. R. Boyd et al., "Biotransformation of Unsaturated Heterocyclic Rings by Pseudomonas putida to Yield cis-Diols", *J. Chem. Soc. Chem. Commun*, (1993), pp. 49–51.

M. K. Trower et al., "Xenobiotic Oxidation by Cytochrome P–450–Enriched Extracts of Streptomyces Griseus", *BBRC*, (1988), 157:3, pp. 1417–1422.

W. R. Abraham et al., "Hydroxy–(Methylbutenynyl)–Benzoic Acid and Derivatives from Curvularia Fallax", *Phytochem*, (1990) 29:8, pp. 2641–2644.

J. B. Jones, "Enzymes in Organic Synthesis", *Tetrahedron*, (1986) 42:13, pp. 3351–3403.

D. G. Smith et al., "Pyrrole Analogues of the Pyrrolidinone Moiety of the Potassium Channel Activator Cromakalim as Relaxants of Guinea Pig Trachealis", *Bioorg. & Med. Chem. Lett.*, (1992) 2:12, pp. 1595–1598.

*Primary Examiner*—Marian C. Knode
*Assistant Examiner*—S. Saucier
*Attorney, Agent, or Firm*—Ellen K. Park

[57] ABSTRACT

An enzymatic process for the preparation of chiral epoxides, monohydroxy or dihydroxy compounds of formula

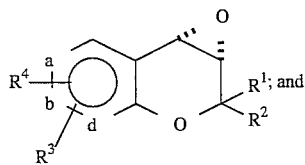

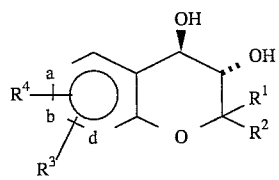

by the stereoselective epoxidation or hydroxylation of benzopyrans of formula

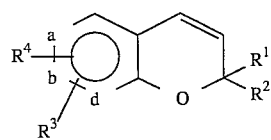

or resolution of compounds of formula

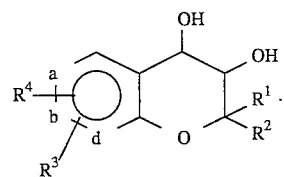

The compounds of formula I and II are intermediates useful in the preparation of pyranyl cyanoguanidine derivatives.

3 Claims, No Drawings

METHOD OF CHIRAL EPOXIDATION OF BENZOPYRAN OR PYRANOPYRIDINE DERIVATIVES USING MICROORGANISMS

This application is a continuation-in-part of U.S. Application Ser. No. 079,712, filed Jun. 18, 1993, now abandoned.

FIELD OF THE INVENTION

The instant invention relates to a novel enzymatic process for the stereoselective preparation of chiral epoxide compounds from benzyopyran compounds. The instant invention thus relates to the stereoselective epoxidation or hydroxylation of benzopyran compounds to time chiral epoxide or the corresponding chiral mono or dihydroxy compounds.

SUMMARY OF THE INVENTION

In accordance with the instant invention, a novel process is provided for preparing a chiral epoxide of formula

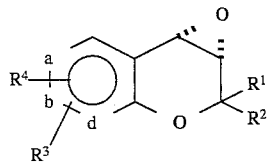

and/or a (+)-trans dihydroxy compound of formula

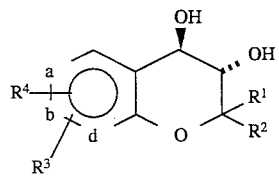

As used in formula I and II and throughout the specification, the symbols have the following meanings:

- a, b, and d are all carbon atoms or one of a, b and d is a nitrogen atom or —NO— and the others are carbon atoms;
- $R^1$ and $R^2$ are independently hydrogen, alkyl or arylalkyl; or $R^1$ and $R^2$ taken together with the carbon atom to which they are attached form a 5- to 7-membered carbocyclic ring;
- $R^3$ is hydrogen, alkyl, haloalkyl, alkenyl, alkynyl, cycloalkyl, arylalkyl, cycloalkylalkyl,—CN,—NO$_2$, —COR, COOR, —CONHR, —CONRR', —CF$_3$, S—alkyl, —SOalkyl, —SO$_2$alkyl,

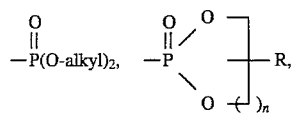

halogen, amino, substituted amino, OH, —O—alkyl, —OCF$_3$, —OCH$_2$CF$_3$, —OCOalkyl, —OCONRalkyl, —NRCO alkyl, —NRCOOalkyl or —NRCONRR' wherein R and R' in each of the above groups is independently hydrogen, alkyl, haloalkyl, aryl, arylalkyl, cycloalkyl, or (cycloalkyl)alkyl;
- $R^4$ is hydrogen, alkyl,—OH, —O—alkyl, amino, substituted amino,—NHCOR,—CN or —NO$_2$; and n is an integer of 1 to 3.

The instant process comprises the step of treating a compound of formula

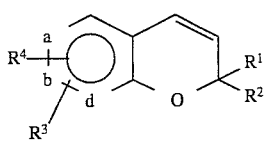

with an enzyme or microorganism capable of catalyzing the stereoselective epoxidation of the compounds of formula III to form the chiral epoxide of formula I or the stereoselective hydroxylation to form the chiral dihydroxy compound of formula II.

The invention also includes the process of preparing the trans-(+)-diols of the formula II, comprising the step of treating a racemic trans diol of formula

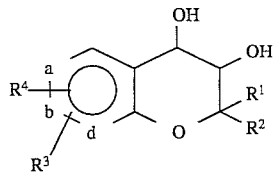

with a lipase or esterase or microorganism capable of producing said lipase or esterase to resolve the racemic diols.

The compounds of formula I are key intermediates in the preparation of compounds having potassium channel activating activity. The chiral dihydroxy compounds of formula II may be converted to the chiral epoxide of formula I, which may then be utilized to prepare compounds having potassium channel activating activity.

The above process may also be used to form the chiral monohydroxy compounds of the formula

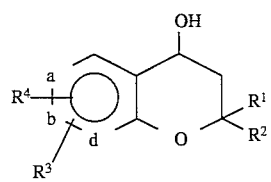

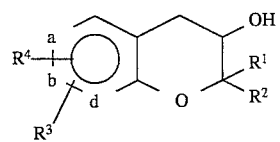

DETAILED DESCRIPTION OF THE INVENTION

The following definitions apply to the terms as they are used throughout the specification (unless they are otherwise limited in specific instances) either individually or as part of a larger group.

The term "alkyl" refers to straight and branched chain hydrocarbons, containing 1 to 8 carbons in the normal chain, preferably 1 to 5 carbons such as methyl, ethyl, propyl, butyl, pentyl, the various branched chain isomers thereof such as isopropyl, t-butyl, isobutyl, 4,4-dimethyl-pentyl, 2,2,4-trimethylpentyl, and the like as well as such groups including a halo-substituent, such as F, Br, Cl or I such as CCl₃ or CF₃, an alkoxy substituent, an aryl substituent, an alkyl-aryl substituent, a haloaryl substituent, a cycloalkyl substituent, an alkyl-cycloalkyl substituent, a hydroxy substituent, an alkylamino substituent, an alkanoylamino substituent, an arylcarbonylamino substituent, a nitro substituent, a cyano substituent, a thiol substituent or an alkylthio substituent.

The terms "alkoxy" and "alkylthio" refer to such alkyl groups as described above linked to an oxygen atom or sulfur atom respectively.

The term "alkenyl" refers to such groups as described above for alkyl, further containing at least one carbon to carbon double bond.

The term "alkynyl" refers to such groups as described above for alkyl, further containing at least one carbon to carbon triple bond.

The term "cycloalkyl" as employed herein includes saturated cyclic hydrocarbon groups containing 3 to 7 ring carbons with cyclopropyl, cyclopentyl and cyclohexyl being preferred.

The term "halogen" or "halo" refers to chlorine, bromine, iodine and fluorine.

The term "aryl" refers to phenyl, 1-naphthyl, 2-naphthyl or mono substituted phenyl, 1-naphthyl, 2-naphthyl wherein said substituents is alkyl of 1 to 4 carbons, alkylthio of 1 to 4 carbons, alkoxy of 1 to 4 carbons, halo, nitro, cyano, hydroxy, amino, —NH—alkyl wherein alkyl is of 1 to 4 carbons, —N(alkyl)₂ wherein alkyl is of 1 to 4 carbons, —CF₃,

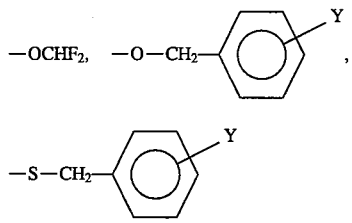

(where Y is hydrogen, alkyl of 1 to 4 carbons, alkoxy of 1 to 4 carbons, alkylthio of 1 to 4 carbons, halo, hydroxy or —CF3), —O—CH₂—cycloalkyl, or —S—CH₂—cycloalkyl, and di-substituted phenyl, 1-naphthyl, 2-naphthyl wherein said substituents are selected from methyl, methoxy, methylthio, halo, —CF₃, nitro, amino, and —OCHF₂. Preferred aryl groups include unsubstituted phenyl and monosubstituted phenyl wherein the substituents are nitro, halo, —CF₃, alkyl, cyano or methoxy.

The term "heterocyclo" refers to fully saturated or unsaturated rings of 5 or 6 atoms containing one or two O and S atoms and/or one to four N atoms provided that the total number of hetero atoms in the ring is 4 or less. The hetero ring is attached by way of an available carbon atom. Preferred monocyclic hetero groups include 2- and 3-thienyl, 2- and 3-furyl, 2-, 3- and 4-pyridyl, and imidazolyl. The term hetero also includes bicyclic rings wherein the five or six membered ring containing O, S and N atoms as defined above is fused to a benzene ring and the bicyclic ring is attached by way of an available carbon atom. Preferred bicyclic hetero groups include 4, 5, 6, or 7-indolyl, 4, 5, 6 or 7-isoindolyl, 5, 6, 7 or 8-quinolinyl, 5, 6, 7 or 8-isoquinolinyl, 4, 5, 6, or 7-benzothiazolyl, 4, 5, 6 or 7-benzoxazolyl, 4, 5, 6 or 7-benzimidazolyl, 4, 5, 6 or 7-benzoxadiazolyl and 4, 5, 6 or 7-benzofuranzanyl.

The term heterocyclo also includes such monocyclic and bicyclic rings wherein an available carbon atom is substituted with a lower alkyl of 1 to 4 carbons, lower alkylthio of 1 to 4 carbons, lower alkoxy of 1 to 4 carbons, halo, nitro, keto, cyano, hydroxy, amino, —NH—alkyl wherein alkyl is of 1 to 4 carbons, —N(alkyl)₂ wherein alkyl is of 1 to 4 carbons, —CF₃, or —OCHF₂ or such monocyclic and bicyclic rings wherein two or three available carbons have substituents selected from methyl, methoxy, methylthio, halo, —CF₃, nitro, hydroxy, amino and —OCHF₂.

The term "substituted amino" refers to a group of the formula —NZ₁Z₂ wherein Z₁ is hydrogen, alkyl, cycloalkyl, aryl, arylalkyl, (cycloalkyl)alkyl and Z₂ is alkyl, cycloalkyl, aryl, arylalkyl, (cycloalkyl)alkyl or Z₁ and Z₂ taken together with the nitrogen atom to which they are attached are 1-pyrrolidinyl, 1-piperidinyl, 1-azepinyl, 4-morpholinyl, 4-thiamorpholinyl, 1-piperazinyl, 4-alkyl-1-piperazinyl, 4-arylalkyl- 1 -piperazinyl, 4-diarylalkyl- 1-piperazinyl, 1 -pyrrolidinyl, 1-piperidinyl or 1-azepinyl substituted with alkyl, alkoxy, alkylthio, halo, trifluoromethyl or hydroxy.

The term "stereoselective epoxidation" refers to the preferential epoxidation of the 1aS-cis enantiomer of the compound of formula III relative to its 1aR-cis enantiomer. The term "stereoselective hydroxylation" refers to the preferential hydroxylation to form the optically active dihydroxy compounds of formula II.

In accordance with the present invention, it has been found that, in the presence of one or more epoxidizing enzymes or microorganisms producing same, the stereoselective epoxidation of the compounds of the formula III is achieved. The enzymatic epoxidation process of the present invention is advantageous in that it provides high yields of the chiral epoxides of the compounds of formula I with high optical purity. When the reaction is carried out at ambient temperature, for example, an optical purity of greater than about 80% may be obtained with a reaction yield of greater than about 50%. Preferably, an optical purity of greater than 85% with a reaction yield of greater than about 60% may be obtained.

In addition to the chiral epoxide, the present process also comprises the stereoselective hydroxylation of compounds of formula III to produce the chiral trans-dihydroxy compounds of formula II.

Further, the chiral dihydroxy compounds of formula II may be prepared from the racemic trans diols of formula IIa by treatment of the racemic trans diols with lipase, esterase or microorganism capable of supplying said lipase or esterase.

The racemic trans diols of formula IIa are obtained by dissolving racemic epoxide of formula

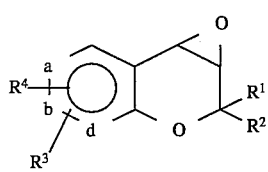

Ia in an organic solvent such as tetrahydrofuran in the presence of water and catalytic amounts of a mineral acid such as perchloric acid.

Compounds of formula Ia can be prepared by methods described in the literature, such as by J. M. Evans et al., *J. Med. Chem.*, (1983), 26, 1582; J. M. Evans et al., *J. Med. Chem.*, (1986), 29, 2194; R.W. Lang et al., *Helvetica Chimica Acta*, (1988), 71,596; European patent 0205292 A2 and PCT patent 87/07607.

The starting materials of formula III and methods for obtaining them are known (Evans et al., *J. Med. Chem.*, (1983), 26, 1582 and *J. Med Chem.*, (1986), 29, 2194).

The present processes are preferably carried out in an aqueous system such as water or an aqueous buffer.

Any enzyme or microorganism having the ability to catalyze the stereoselective epoxidation or stereoselective hydroxylation of the compounds of formula III as described herein may be employed in the present processes. Two or more as well as single species of microorganism may be employed.

Various enzymes, regardless of origin or purity, are suitable for use in the present invention. The enzyme may, for example, be in the form of animal or plant enzymes or mixtures thereof, cells of microorganisms, crushed cells, extracts of cells, or of synthetic origin.

The enzyme employed, when derived from a microorganism, may be derived either by extracellular expression of the enzyme by the microorganism or by separating intracellularly-prepared enzyme from cellular materials. The enzyme employed may, for example, be an enzyme isolated from a microorganism such as by homogenizing cell suspensions, followed by disintergration, centrifugation, DEAE-cellulose chromatography, ammonium sulfate fractionation, chromatography using gel filtration media such as Sephacryl (cross-linked co-polymer of allyl dextran and $N,N^1$-methylene bisacrylamide) chromatography, and ion exchange chromatography such as Mono-Q (anion exchanger which binds negatively charged biomolecules through quaternary amine groups) chromatography. The microbial genera and species discussed below with respect to the use of microorganisms are exemplary of microbial enzyme sources.

Suitable enzymes for the stereoselective epoxidation or stereoselective hydroxylation include those enzymes referred to as epoxidase, alkane epoxidase, monooxygenase, alkane monooxygenase, dioxygenase, p-450 monooxygenase, or epoxide hydratase. Exemplary, commercially available enzymes suitable for use in the present invention include microsomal enzyme preparations, alkene epoxidizing and alkane hydroxylation enzymes, cytochrome p-450 enzymes, monooxygenase, dioxygenase, and hydroxylase enzymes.

The epoxidation and hydroxylation enzyme (cells or cellular materials) may be employed in the free state or immobilized on a support. The enzyme may, for example, be adsorbed onto a suitable cartier, e.g., oxirane-acrylic beads (Eupergit C), diatomaceous earth (porpous Celite Hyflo Supercel), microporous polyproplyene (Enka Accurel® polypropylene powder), or a nonionic polymeric adsorbent such as Amberlite® XAD-2 (polystyrene) or XAD-7 (polyacrylate) from Rohm and Haas Co. Immobilizing the enzyme has the effects of controlling the enzyme particle size, and preventing aggregation of the enzyme particles. Additionally, and preferably, immobilized enzymes may be readily reused in the instant process. Adsorption onto a support such as Celite Hyflo Supercel may be accomplished, for example, by precipitating an aqueous solution of the enzyme with cold acetone in the presence of the support followed by vacuum drying, or in case of a nonionic polymeric adsorbent, incubating enzyme solutions with adsorbent on a shaker for a desired time, removing excess solution and drying the enzyme-adsorbent resins under vacuum. It is particularly preferred to employ enzyme immobilized on an oxirane-acrylic bead support such as Eupergit C in the process of the instant invention.

With respect to the use of microorganisms, the processes of the present invention may be carried out using any microbial cellular material having the ability to catalyze the stereoselective epoxidation or hydroxylation of the compounds of formula III as described herein. In addition, any microorganism capable of supplying lipase or esterase for the resolution of compounds of formula IIa to the chiral diols of formula II may be utilized. The cells may be used in the form of intact wet cells or dried cells such as lyophilized, spray-dried or heat-dried cells. Cells may also be used in the form of treated cell material such as ruptured cells or cell extract.

Suitable microorganisms include genera from bacteria, yeasts and fungi such as Achromobacter, Acinetobacter, Actinomyces, Alkaligenes, Arthrobacter, Aspergillus, Azotobacter, Bacillus, Brevibacterium, Candida, Corynebacterium, Cunninghamella, Curvularia, Diplodia, Flavobacterium, Fusarium, Geotrichum, Hansenula, Helicostylum, Kloeckera, Methylococcus, Methylomonas, Methylosinus, Mortierella, Mucor, Mycobacterium, Nitrosomonas, Nocardia, Penicillium, Pichia, Pseudomonas, Rhizopus, Rhodococcus, Rhodopseudomonas, Rhodotorula, Saccharomyces, Streptomyces, Torulopsis, Trichoderma or Xanthomonas.

The use of microorganisms of the genera Corynebacterium, Rhodococcus and Mycobacterium are preferred for the epoxidation or hydroxylation reactions.

In addition, the following species are preferred for the epoxidation or hydroxylation reactions: *Acinetobacter calcoaceticus, Arthrobacter rubellus, Arthrobacter simplex, Brevibacterium fuscum, Candida albicans, Candida lipolytica, Corynebacterium alkanum,* Corynebacterium sp., *Cunninghamella echinulata, Curvularia lunata, Diplodia gossypina, Geotrichum candidum, Hansenula fabianii, Hansenula polymorpha, Helicostylum elegans, Methylococcus capsulatus, Methylosinus trichosporium, Mortierella alpina, Mortierella ramanniana, Mucor hiemalis, Mycobacterium vacca, Nitorsomonas europea, Nocardia autotrophica, Nocardia corallina, Nocardia globerula, Nocardia meditteranei, Nocardia restricta, Nocardia salmonicolor, Pichia methanolica, Pichia pastoris, Pseudomonas fluorescans, Pseudomonas oleovorans, Pseudomonas putida, Rhodococcus equi, Rhodococcus erythropolis, Rhodococcus fascians, Rhodococcus rhodochrous, Torulopsis polysporium* and *Torulopsis glabrata*.

Most preferred microorganisms for the epoxidation or hydroxylation reactions include the following strains: *Arthrobacter rubellus* (ATCC 21495), *Corynebacterium alkanum* (ATCC 21194), Corynebacterium sp. (ATCC 43752), *Cunninghamella echinulata* (ATCC 9244), *Curvularia lunata* (ATCC 12017), *Diplodia gossypina* (ATCC 10936), *Hansenula fabianii* (ATCC 58045), *Hansenula polymorpha* (ATCC 26012), *Helicostylum elegans* (ATCC 12745), *Mortierella ramanniana* (ATCC 38191 and ATCC 24786), *Mucor hiemalis* (ATCC 89778), *Mycobacterium vacca* (ATCC 29678), *Nocardia corallina* (ATCC 31338), *Nocardia globerula* (ATCC 21505), *Pseudomonas putida* (ATCC 11172 and ATCC 23287), *Pseudomonas oleovorans* (ATCC 9347) and *Rhodococcus erythropolis* (ATCC 4277).

While any microorganism, including those listed above for the epoxidation or hydroxylation reactions, which are capable of providing a lipase or esterase which resolves the racemic trans diol may be utilized, the microorganisms Candida, Pseudomonas or Geotrichum are preferred for the resolution reactions.

The use of genetically engineered organisms is also contemplated. The host cell may be any cell, e.g. *Escherichia coli*, modified to contain a plasmid bearing enzymes that catalyzes the epoxidation or hydroxylation reactions or that resolves the substrates.

The term "ATCC" as used herein refers to the accession number of the American Type Culture Collection, 12301 Parklawn Drive, Rockville, Md. 20852, the depository for the organism referred to.

When microorganisms are employed for the processes of this invention, the reactions may, for example, be carried out as a single-step process comprising simultaneous fermentation and transformation of the compounds of formula III or IIIa, or resolution of compounds of formula IIa or as a two-step fermentation and subsequent transformation process.

In a single-step process, the microorganisms used may be grown in an appropriate medium containing carbon and nitrogen sources. The starting formula III, IIIa, or IIa compounds may be added to the microbial cultures, and transformation of the formula III, IIIa, or IIa compounds to the formulae I or II compounds continued until a desired conversion is obtained.

In a two-step process, microorganisms may, in the first step, be grown in an appropriate medium by fermentation exhibiting the desired epoxidizing enzyme activity. The cells may then be harvested and suspended, for example, in an appropriate buffered solution to prepare cell suspensions. The formula III compounds may be mixed with the microbial cell suspensions, and the transformation of formula III compounds to the desired product catalyzed by the cell suspensions. The reaction may be continued until a desired conversion of the formula III compounds is obtained.

Culture media may be employed which provide nutrients necessary for the growth of the microbial cells. A typical medium for growth includes necessary carbon sources, nitrogen sources, and trace elements.

Carbon sources include sugars such as maltose, lactose, glucose, fructose, glycerol, sorbitol, sucrose, starch, mannitol, and the like; organic acids such as sodium acetate, sodium citrate, and the like; amino acids such as sodium glutamate, and the like; alcohols such as ethanol, propanol, and the like. The carbon source may be added during transformation. Also, formula III compounds may be added as an inducer during growth of the microorganisms.

Nitrogen sources include N-Z Amine A, corn steep liquor, soy bean meal, beef extracts, molasses, baker's yeast, tryptone, nutrisoy, sodium nitrate, ammonium sulfate, and the like.

Trace elements include phosphates, magnesium, manganese, calcium, cobalt, nickel, iron, sodium, and potassium salts.

Typical preferred media are as follows:

| Medium 1 | |
|---|---|
| Beef extract | 5 g |
| Peptone | 7.5 g |
| NaCl | 2.5 g |
| Glucose | 5 g |
| Yeast extract | 1.5 g |
| Malt extract | 1.5 g |
| Ucon antifoam* | 0.1 g |
| Water | 1 Liter |
| Medium 2 | |
| Cerelose | 22 g |
| Yeast Extract | 10 g |
| Malt Extract | 10 g |
| Peptone | 1 g |
| Water | 1 Liter |
| | pH = 6.8 |

*Polysiloxanes

Microorganisms may be grown in Medium 1, for example, for 24 to 48 hours at 280 rpm agitation and 28° C. to 30° C., for inoculum development. A fermentor containing Medium 2 (10%) may then be inoculated with microorganisms grown in Medium 1. An exemplary arrangement for fermentation of approximately 190 L of Medium 2 may, for example, include a 250 L fermentor which is equipped with three Rushton (flat-blade turbine) impellers, a sparger, a pH controller, a dissolved oxygen (DO) meter, a temperature controller, a foam sensor with automatic antifoam addition, and inlet and exhaust air filters.

The efficiency of the process may be affected by both the initial amount of formula III or IIa substrate used and by the timing and amount of substrate added during the process. Substrate may be added batchwise, for example, every one to 12 hours, or continuously during the transformation process by growing cells in a one-step fermentation, or by cell-suspensions of microorganisms as in a two-step fermentation/ transformation process.

While it is desirable to use the least amount of enzyme possible, the amount of enzyme required will vary depending upon the specific activity of the enzyme employed. The enzyme is, in general, preferably added to the reaction solution in an amount of from about 0.01 to about 10 mg of enzyme per mg of formula III or IIa compound, most preferably, from about 0.1 to about 2 mg enzyme per mg of formula III or IIa compound.

Preferred initial concentrations of formula III or IIa substrate are those between about 10 mg/mL and about 100 mg/mL, particularly between about 5 mg/mL and 50 mg/mL, based on cell concentration. Additional substrate is preferably added in amounts such as those between about 5 mg/mL and about 10 mg/mL.

The pH of the medium may be maintained between about 4.0 and about 9.0, preferably between about 5.5 and about 7.0, during growth of microorganisms and during the transformation process.

Buffers such as tris-HCl phosphates, sodium acetate and the like may be used to prepare suspensions of microbial cells to conduct the transformation process.

The temperature of the reaction mixture is a measure of the heat energy available for the transformation process. The reaction temperature may be selected and maintained to ensure that there is sufficient energy available for the process. A temperature range from about 15° C. to 60° C., especially from about 20° C. to 35° C., is preferred for the transformation.

The agitation and aeration of the reaction mixture affects the amount of oxygen available during the transformation process which may be conducted, for example, in shake-flask cultures or fermenter tanks during growth of microorganisms in a single-step or two-step process. An agitation range of from about 50 to about 1000 rpm is preferable, with a range of from about 50 to about 500 rpm being preferred. Aeration rates of from about 1 to about 5 volumes of air per volume of media per minute (i.e., 1 to 5 v/vt) are preferred.

The reaction time may be appropriately varied depending upon the amount of enzyme used and its specific activity. Reaction times may be reduced by increasing the reaction temperature and/or increasing the amount of enzyme added to the reaction solution.

The optimum reaction time for the transformation process generally ranges from about 12 to about 168 hours, preferably 24 to 120 hours, measured from the time of initially treating the substrate (formula III or IIa compound) with a microorganism to the time at which a desired conversion of formula III or IIa compound to formula I or II is achieved.

The compounds of formulae I and II may be purified by known methodologies such as extraction, distillation, crystallization, column chromatography, and the like.

The compounds of formula I and formula II (via conversion to formula I) may be utilized to prepare compounds having potassium channel activation activity.

The chiral dihydroxy compounds of formula II may be converted to the epoxides of formula I by reaction with a R-sulfonyl halide (where R is an alkyl such as methyl or $CF_3$, or an aryl) such as methanesulfonyl chloride or p-toluenesulfonyl chloride to form compounds of formula

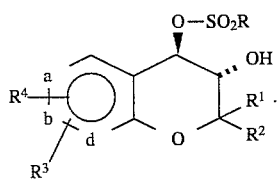

V

Subsequent treatment with an organic base such as a tertiary amine (for example: 1,8-diazabicyclo[5.4.0]undec-7-ene, 1,5-diazabicyclo-[4.3.0]-non-5-ene, triethylamine) in an organic solvent such as dimethylformamide or tetrahydrofuran or subsequent treatment with an inorganic base such as potassium carbonate in a solvent such as dimethylformamide, acetone, methylethyl ketyone or tetrahydrofuran produces the chiral epoxide of formula I.

Exemplary potassium channel activators include pyranyl cyanoguanidine derivatives of the formula

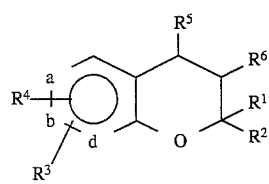

VI where a, b, d, $R^1$, $R^2$, $R^3$ and $R^4$ are as defined for formula I and

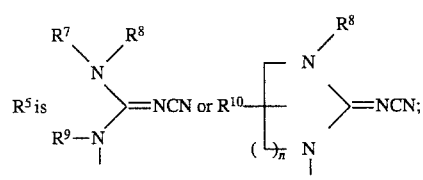

$R^6$ is hydrogen, hydroxy or

$R^7$ and $R^8$ are independently hydrogen, alkyl, alkenyl, aryl, (heterocyclo)alkyl, heterocyclo, arylalkyl, cycloalkyl, (cycloalkyl)alkyl or substituted alkyl wherein the substituents include alkoxy, alkylthio and substituted amino; or $R^7$ and $R^8$ taken together with the nitrogen atom to which they are attached form 1-pyrrolidinyl, 1-piperidinyl, 1-azepinyl, 4-morpholinyl, 4-thiamorpholinyl, 1-piperazinyl, 4-alkyl-1-piperazinyl or 4-arylalkyl-1-piperazinyl, wherein each of the so-formed groups can be substituted with alkyl, alkoxy, alkylthio, halogen or trifluoromethyl; and $R^9$ and $R^{10}$ are independently hydrogen, alkyl, alkenyl, aryl, arylalkyl, cycloalkyl or (cycloalkyl)alkyl; or $R^{10}$ can be an aryl group fused to 2 carbon atoms of the cyanoguanidine ring portion.

Compounds of formula VI and methods of preparing such compounds are disclosed in U.S. Pat. No. 5,140,031, the disclosure of which is incorporated by reference herein.

Preferred compounds of formula VI are those

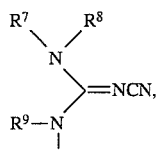

where $R^5$ is
and $R^7$ is mono- or di- substituted phenyl.

An exemplary method of preparing the compounds of formula VI where $R^5$ is

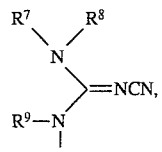

using the intermediates of formula I prepared as disclosed herein includes treatment of compounds of formula I with an amine such as ammonia to provide the amines of formula

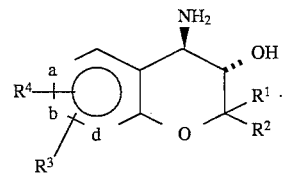

VII

The amine of formula VII is then treated with an isocyanide dihalide of the formula $R^8$—N=C(X)$_2$  (VIII)

(where $R^8$ is other than hydrogen and X is a halogen, preferably chlorine) in solvent such as dichloromethane, 1,2 dichloroethane, acetonitrile, ethyl acetate or preferably an alcoholic solvent such as isopropyl alcohol or ethanol, containing a tertiary amine such as diisopropylethylamine to form a compound of formula

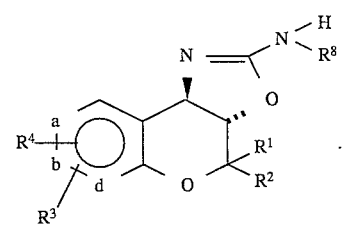

IX

Alternatively treatment of compounds of formula VII with an isothiocyanate of the formula $R^8$—N=C=S  (X)

such as 4-chlorophenylisothiocyanate provides a thiourea of formula

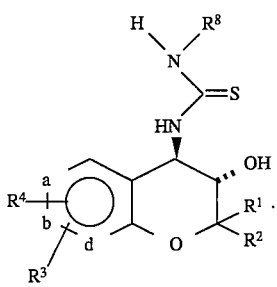

XI

Subsequent treatment of the thiourea of formula XI with a carbodiimide such as 1-ethyl-3-(3-dimethylaminopropyl)cabodiimide hydrochloride (WSC) provides the compounds of formula IX.

Treatment of compounds of formula IX with cyanamide in a solvent such as alcohol or acetonitrile, optionally in the presence of a base such as triethylamine or 2,6-lutidine provides the compounds of formula VI where $R^6$ is hydroxy. Compounds of formula VI where $R^6$ is —OC(O)CH$_3$ may be prepared by acetylation of the compounds of formula VI where $R^6$ is hydroxy. Compounds of formula VI where $R^6$ is hydrogen may be prepared by dehydration of the compounds of formula VI where $R^6$ is hydroxy, followed by reduction by procedures known in the art.

Preferred compounds of formula VIII include substituted alkyl and aryl isocyanide dihalides such as substituted phenyl isocyanide dichlorides. The most preferred compounds of formula VIII is 4-chlorophenyl isocyanide dichloride. Substituted alkyl and aryl isocyanide dihalides are known (E. Kühle, "Carbonic Acid Derivatives from Formamides", *Angew, Chem. Int, Ed.*, (1962), 1,647–652; D. Ferchland et al., "Process for the Preparation of Aryl Isocyanide-Dichlorides", U.S. Pat. No. 4,401,603; and E. Kühle et al., "New Methods of Preparative Organic Chemistry-Reactions of Isocyanide Dihalides and their Derivatives", *Angew, Chem. Int. Ed.*, (1969), 8, 20–34).

The following examples and preparations describe the manner and process of making and using the preferred embodiments of the invention and are illustrative rather than limiting. It should be understood that there may be other embodiments which fall within the spirit and scope of the invention as defined by the claims appended hereto.

EXAMPLE 1

The substrate for this example was the compound having the formula

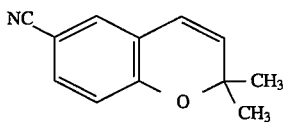

XII and the name 2,2-dimethyl-2H-1-benzopyran-6-carbonitrile. The desired product was the compound having the formula

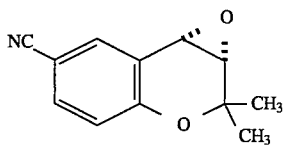

XIII and the name (1αS-cis) -1α,7β-Dihyro-2,2-dimethyl-2H-oxireno[c][-1]benzopyran-6- carbonitrile.

The microorganism Corynebacterium sp. (ATCC 43752) was maintained in a vial in liquid nitrogen. For the development of inoculum, one vial was inoculated into 100 mL of medium 1 in a 500-mL flask and incubated at 28° C. and 280 rpm on a shaker for 48 hours. After growth of the microorgansim, 10 mL of culture was inoculated into a 500-mL flask containing 100 mL of medium 2 and incubated at 28° C. and 250 rpm on a shaker.

Cells were harvested and suspended in 10 mM potassium phosphate buffer pH 6.0. 10mL of 20% w/v cell-suspensions were prepared. Cell-suspensions were supplemented with 10 mg of substrate (compound XII) and 50 mg of glucose and the transformations were conducted at 28° C., 150 rpm for 48 hours. One volume of sample was taken and extracted with four volumes of toluene: tet. butyl methyl ether, 1:1 mixture and the separated organic phase was filtered through a 0.2 mm LID/x filter and collected.

Samples (toluene: tet. butylmethylether, 1:1 mixture) were analyzed for substrate and product concentration by gas chromatography.

An HP ultra-2 column (25 meter length) was used. The injection temperature was 250° C., the detection temperature was 250° C., and the oven temperature was 205° C. The retention times for substrate (compound XII) was 2.6 minutes and the product (compound XIII) was 3.4 minutes.

The separation of the two enantiomers of the racemic epoxide was achieved on a chiralpak AD column. The mobile phase consisted of hexane:ethanol 95:5 mixture. The flow rate was 1 mL/minute and the detection wavelength was 254 nm. The refractive index detector (HP 1047A) was also used. The retention times for the desired enantiomer (compound XIII) was 15 minutes and the undesired enantiomer was 13 minutes. The reaction yield of compound XIII was 65% having an optical purity of 90%.

Experimental results obtained using other microorganisms grown on medium 2 and following the procedure of Example 1 are shown in Table 1 below.

TABLE 1

| Microorganism | Reaction Yield Compound XIII (%) | Optical Purity Compound XIII (%) |
| --- | --- | --- |
| Pseudomonas putida ATCC 23287 | 35 | 85 |
| Pseudomonas oleovorans ATCC 29347 | 30 | 82 |
| Corynebacterium alkanum ATCC 21194 | 45 | 80 |
| Curvularia lunata ATCC 12017 | 20 | 78 |
| Helicostylum elegans ATCC 12745 | 30 | 85 |
| Diplodia gossypina ATCC 10936 | 35 | 75 |
| Nocardia corallina ATCC 31338 | 60 | 80 |
| Arthrobacter rubellus ATCC 21495 | 25 | 82 |
| Cunninghamella echinulata ATCC 9244 | 20 | 90 |
| Mucor hiemalis ATCC 89778 | 25 | 88 |
| Rhodococcus erythropolis ATCC 4277 | 60 | 88 |
| Hansenula polymorpha ATCC 26012 | 50 | 88 |
| Mortierella ramanniana ATCC 24786 | 60 | 75 |

EXAMPLE 2

The substrate for this example was the compound of the formula XII having the name 2,2-dimethyl 2H-1-benzopyran-6-carbonitrile (as in Example I). The desired products were (compounds of formulae XIV, XV and XVI as below):

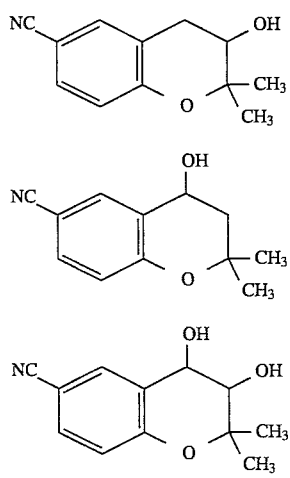

Compound XIV

Compound XV

Compound XVI having the names:

Compound XIV: 4-Hydroxy-2,2-dimethyl-6-carbonitrile-2H-1-benzopyran-3-ol;

Compound XV: 3-Hydroxy-2,2-dimethyl-6-carbonitrile-2H-1-benzopyran-4-ol; and

Compound XVI: (+)-trans-3,4-Dihydroxy-3,4-dihydro-2,2-dimethyl-2H-1-benzopyran-6-carbonitrile.

Microorganisms listed in Table 2 below were grown as described in Example 1. The reactions were carried out as described in the Example 1 using compound XII as the substrate. Products (compound XIV, XV and XVI) were analyzed by GC assays and the optical purity was determined by Chiral HPLC assays. Experimental results obtained are shown in Table 2 below.

TABLE 2

| Microorganism | Reaction Yield Compound XIV (%) | Reaction Yield Compound XV (%) | Reaction Yield Compound XVI (%) | Optical Purity Compound XVI (%) |
|---|---|---|---|---|
| Corynebacterium sp. ATCC 43752 | 2 | 3 | 80 | 92 |
| Pseudomonas putida ATCC 23287 | 1.5 | 4 | 70 | 91 |
| Pseudomonas oleovorans ATCC 29347 | 0.5 | 5 | 65 | 90 |
| Corynebacterium alkanum ATCC 21194 | 0.2 | 2 | 45 | 88 |
| Curvularia lunata ATCC 12017 | 0.4 | 6 | 20 | 85 |
| Helicostylum elegans ATCC 12745 | 0.6 | 5 | 15 | 80 |
| Diplodia gossypina ATCC 10936 | 1.0 | 4 | 40 | 90 |
| Nocardia corallina ATCC 31338 | — | 3 | 65 | 75 |
| Arthrobacter rubellus ATCC 21495 | — | 2 | 40 | 91 |
| Cunninghamella echinulata ATCC 9244 | — | 6 | 55 | 92 |
| Mucor hiemalis ATCC 89778 | — | 4 | 60 | 88 |
| Rhodococcus erythropolis ATCC 4277 | 0.4 | 2 | 70 | 92 |
| Hansenula polymorpha ATCC 26012 | 0.8 | 5 | 50 | 90 |
| Mortierella ramanniana ATCC 24786 | 1.0 | 3 | 81 | 76 |

EXAMPLE 3

The substrate for this example was the compound of the formula XII having the name 2,2-dimethyl-2H-1-benzopyran-6-carbonitrile (as in Example 1). The desired product was the compound of the formula XIII and the name (1αS-cis) -1α,7β-dihydro-2,2 benzopyran-6-carbonitrile (as in Example 1).

The microorganisms listed in Table 3 were maintained in a vial in liquid nitrogen. For development of inoculum, one vial was inoculated into 100 mL of medium 1 in a 500-mL flask and incubated at 28° C. and 280 rpm on a shaker for 48 hours. After growth of the microorganism, 10 mL of culture was inoculated into a 500-mL flask containing 100 mL of medium 2 containing 0.2% substrate (compound XII) and incubated at 28° C. and 250 rpm on a shaker.

After 24 hours of growth, medium 2 (50 mL) was supplemented with 50 mL of culture (grown for 24 hours) and 1 mg/mL of compound XII was added to the medium. The epoxidation reaction was further continued at 280° C., 250 rpm on a shaker for 96 hours. The concentration of product XIII and optical purity of product XIII were determined as described in the Example 1. Experimental results obtained are shown in Table 3 below.

TABLE 3

| Microorganism | Reaction Yield Compound XIII (%) | Optical Purity Compount XIII (%) |
|---|---|---|
| Corynebacterium sp. ATCC 43752 | 50 | 91 |
| Pseudomonas putida ATCC 23287 | 30 | 85 |
| Pseudomonas oleovorans ATCC 29347 | 28 | 82 |
| Corynebacterium alkanum ATCC 21194 | 40 | 81 |
| Curvularia lunata ATCC 12017 | 15 | 77 |
| Helicostylum elegans ATCC 12745 | 25 | 82 |
| Diplodia gossypina ATCC 10936 | 30 | 75 |
| Nocardia corallina ATCC 31338 | 45 | 80 |
| Arthrobacter rubellus ATCC 21495 | 15 | 81 |
| Cunninghamella echinulata ATCC 9244 | 10 | 91 |
| Mucor hiemalis ATCC 89778 | 20 | 86 |
| Rhodococcus erythropolis ATCC 4277 | 40 | 85 |
| Hansenula polymorpha ATCC 26012 | 45 | 88 |
| Mortierella ramanniana ATCC 24786 | 42 | 78 |

EXAMPLE 4

The substrate for this example was the compound of formula XII having the name 2,2-dimethyl 2H-1-benzopyran-6-carbonitrile (as in Example 1). The desired products were the compounds of formula XIV, XV and XVI as in Example 2.

The microorganisms listed in Table 4 were grown as described in Example 3 and the reactions were carded out as described in Example 3. The product concentration of compounds XIV, XV and XVI were determined by GC assays. The optical purity of compound XVI was determined by chiral HPLC. Experimental results obtained using various microorgansims are shown in Table 4.

TABLE 4

| Microorganism | Reaction Yield Compound XIV (%) | Reaction Yield Compound XV (%) | Reaction Yield Compound XVI (%) | Optical Purity Compound XVI (%) |
|---|---|---|---|---|
| Corynebacterium sp. ATCC 43752 | 0.4 | 2 | 65 | 91 |
| Pseudomonas putida ATCC 23287 | 0.3 | 3 | 60 | 90 |
| Pseudomonas oleovorans ATCC 29347 | 0.2 | 5 | 55 | 89 |
| Corynebacterium alkanum ATCC 21194 | 0.4 | 2 | 40 | 84 |
| Curvularia lunata ATCC 12017 | 0.1 | 6 | 15 | 81 |
| Helicostylum elegans ATCC 12745 | 0.15 | 4 | 12 | 91 |
| Diplodia gossypina ATCC 10936 | 0.8 | 3 | 35 | 74 |
| Nocardia corallina ATCC 31338 | — | 2 | 60 | 90 |
| Arthrobacter rubellus ATCC 21495 | — | 1 | 38 | 92 |
| Cunninghamella echinulata ATCC 9244 | — | 5 | 50 | 87 |
| Mucor hiemalis ATCC 89778 | — | 4 | 55 | 91 |
| Rhodococcus erythropolis ATCC 4277 | 0.4 | 2 | 65 | 90 |
| Hansenula polymorpha ATCC 21012 | 0.6 | 5 | 45 | 91 |
| Mortierella ramanniana ATCC 24786 | 0.1 | 2 | 83 | 79 |

EXAMPLE 5

Use of Whole Cells: Variation in Reaction Time (Two-Stage Process)

The substrate for this example was the compound of formula XII and the desired product was the compound of formula XIII as described in Example 1.

Cells of Corynebacterium sp. ATCC 43752 were grown in 100 mL of Medium 1 contained in 500-mL flasks. Growth was carried out at 28° C. for 48 hours at 280 rpm. 100 mL of cultures were innoculated into 15 L of Medium 2 contained in a fermentor. Medium 2 was supplemented with 0.2% of compound XII. Growth in the fermentor was carried out at 28° C., 5 liters per minute (LPM) aeration and 500 rpm agitation for 48 hours. Cells were hatwested from the fermentor and used for epoxidation ("biotransformation") of compound XII to compound XIII.

Cells (200 grams) were suspended in 1 liter of 100 mM potassium phosphate buffer, pH 6.0 and homogeneous cell suspensions were prepared. 1 gram of compound XII and 10 grams of glucose were added to the cell suspensions and the biotransformation of compound XII to compound XIII was carried out at 28° C., 160 rpm for 96 hours. After 48 hours, an additional 35 grams of glucose were added and the biotransformation was continued for 96 hours at 28° C., 160 rpm. Samples were prepared and product yield and optical purity were determined as described in Example 1. The results obtained are summarized in Table 5 following.

TABLE 5

| Reaction Time (Hours) | Reaction Yield Compound XIII (%) | Optical Purity Compound XIII (%) |
|---|---|---|
| 24 | 10 | — |
| 48 | 20 | — |
| 72 | 34 | — |
| 96 | 48 | 90 |

EXAMPLE 6

Use of Whole Cells; Variation in Reaction Time (Single-Stage process)

The substrate for this example was the compound of formula XII and the desired product was the compound of formula XIII as described in Example 1.

Cells of Corynabacterium sp. ATCC 43752 were grown in 100 mL of Medium 1 contained in 500-mL flasks. Growth was carded out at 28° C. for 48 hours at 280 rpm. 100 mL of cultures were inoculated into 10 L of Medium 2 contained in a fermentor. Medium 2 was supplemented with 0.2% of compound XII. Growth in the fermentor was carried out at 28° C., 15 liters per minute (LPM) aeration and 500 rpm agitation for 24 hours.

After 24 hours growth in a fermentor, 5L of medium 2 containing 15 grams of compound XII was added to the fermentor and the fermentation/biotransformation was continued at 28° C., 15LPM aeration and 500 rpm agitation for 96 hours. Samples were prepared and product yield and optical purity were determined as described in Example 1. The results obtained are summarized in Table 6 following:

TABLE 6

| Reaction Time (Hours) | Reaction Yield Compound XIII (%) | Optical Purity Compound XIII (%) |
|---|---|---|
| 48 | 20 | — |
| 72 | 30 | — |
| 96 | 45 | 90 |
| 120 | 60 | 92 |

EXAMPLE 7

Use of Whole Cells: Variation in Reaction Time (Single-stage process)

The substrate for this example was the compound of formula XII and the desired product was the compound of formula XVI as described in Example 2.

Cells of Corynebacterium sp. ATCC 43752 were grown in 100 mL of Medium 1 contained in 500-ml flasks. Growth was carried out at 28° C. for 48 hours at 280 rpm. 100 mL of cultures were inoculated into 10 L of Medium 2 contained in a fermentor. Medium 2 was supplemented with 0.2% of compound XII. Growth in the fermentor was carded out at 28° C., 15 liters per minutes (LPM) aeration and 500 rpm agitation for 24 hours.

After 24 hours of growth in a fermentor 5L of Medium 2 containing 15 grams of compound XII was added to the fermentor and the fermentation/biotransformation was continued at 28° C., 15 LPM aeration and 500 rpm agitation for 96 hours. Samples were prepared and product yield and optical purity were determined as described in Example 2. The results obtained are summarized in Table 7 following.

TABLE 7

| Reaction Time (Hours) | Reaction Yield Compound XVI (%) | Optical Purity Compound XVI (%) |
|---|---|---|
| 24 | 15 | — |
| 48 | 25 | — |
| 72 | 40 | — |
| 96 | 65 | — |
| 120 | 80 | 90 |

EXAMPLE 8

Use Of Cell Extracts and Co-factor

The substrate for this example was the compound of formula XII and the desired product was the compound of formula XIII as described in Example 1.

Cells of Corynebacterium sp. ATCC 43572 were grown in Medium 1 and Medium 2 as described in Example 1:

Cells (300 grams) were suspended in 1.5 L of 0.1M potassium phosphate buffer, pH 6.0. The homogenized cell suspensions were disintegrated at 4° C. by a Microfluidizer at 13,000 psi pressure. The disintegrated cell suspension was centrifuged at 10,000 rpm for 30 minutes. The clear supernatant ("cell extract") was used for the biotransformation of compound XII to compound XIII.

One liter of cell extract was supplemented with 0.7 grams of substrate (compound XII), glucose dehydrogenase (500 units), 0.7 mM $NAD^+$ (nicotinamide adenine dinucleotide), and 25 grams of glucose. The reaction was carried out in a pH stat at pH 6.0, 150 rpm agitation, and 28° C. Periodically, samples were taken and analyzed for the reaction yield and optical purity of compound XIII as described in Example 1. The results obtained are those shown in Table 8 following:

TABLE 8

| Reaction Time (Hours) | Reaction Yield Compound XIII g/L | Reaction Yield Compound XIII (%) | Optical Purity Compound XIII (%) |
|---|---|---|---|
| 96 | 0.3 | 45 | 92 |

In the above procedure, the NADH cofactor used for the biotransformation of compound XII to compound XIII was, concurrent with the biotransformation, formed and regenerated using glucose dehydrogenase, $AND^+$, and glucose as shown below:

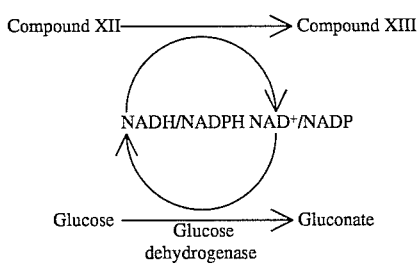

EXAMPLE 9

Use of Cell Extracts and Co-factor

The substrate for this example was the compound of formula XII and the desired product was the compound of formula XVI as described in Example 2.

Cells of CoGnebacterium sp. ATCC 43572 were grown on Medium 1 and Medium 2 as described in Example 3.

Cells (300 grams) were suspended in 1.5 L of 0.1 M potassium phosphate buffer, pH 6.0. The homogenized cell suspensions were disintegrated at 4° C. by a Microfluidizer at 13,000 psi pressure. The disintegrated cell suspension was centrifuged at 10,000 rpm for 30 minutes. The supernatant ("cell extract") was used for the biotransformation of compound XII to compound XVI.

One liter of cell extract was supplemented with 0.7 grams of substrate (compound XII), glucose dehydrogenase (500 units), 0.7 mM $NAD^+$ (nicotinamide adenine dinucleotide), and 25 grams of glucose. The reaction was carded out in a pH stat at pH 6.0, 150 rpm agitation, and 28° C. Periodically, samples were taken and analyzed for the reaction yield and optical purity of compound XVI as described in Example 3. The results obtained are those shown in Table 9 following:

TABLE 9

| Reaction Time (Hours) | Reaction Yield Compound XVI (g/L) | Reaction Yield Compound XVI (%) | Optical Purity Compound XVI (%) |
|---|---|---|---|
| 120 | 0.6 | 85 | 91 |

In the above procedure, the NADH cofactor used for the biotransformation of compound XII to compound XVI was, concurrent with the biotransformation, formed and regenerated using glucose dehydrogenase, $NAD^+$, and glucose as shown below:

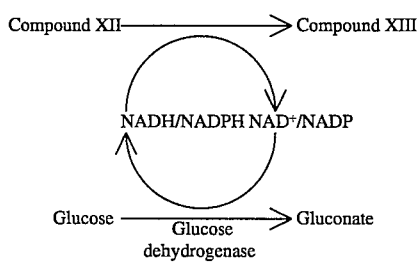

EXAMPLE 10

(+)-trans 3,4-Dihydro-3-4-dihydroxy-2,2-dimethyl-2H-1-benzopyran-6-carbonitrile

6—Carbonitrile-2,2-dimethyl-(3,4)-epoxy-1,2,3,4-tetrahydronapthalene (0.027 mol, 5.0 gin) was dissolved in tetrahydrofuran (12 mL). To this solution was added water (0.5 mL) and one drop of perchloric acid (70%). The reaction mixture was stirred at room temperature for 30 minutes. The progress of the reaction was followed by GC. After all epoxide was converted, water (25 mL) was added and the resulting mixture extracted twice with dichloromethane (25 mL). The organic layer was then washed with 0.7M sodium bicarbonate solution. The organic extract was then dried over anhydrous sodium sulfate. The solvent was removed under reduced pressure to produce 4.8 gm of (+)-trans 3,4-dihydro-3-4-dihydroxyo2,2-dimethyl-2H-1-benzopyran-6-carbonitrile as a white powder (81 M% yield), and 98% chemical purity as analyzed by GC.

1H NMR ($CDCl_3$, 300 MHz): $\delta$1.22 (s, 3H, $CH_3$), 1.45 (s, 3H, $CH_3$), 3.18 (s, 2H, OH), 3.62 (d, J=8.5 Hz, 1H, H-3), 4.68 (d, J=8.5 Hz, 1H, H-4), 6.82 (d, J=10 Hz, 1H, H-8), 7.31 (s, 1H, H-5), 7.4 (d, J=1.1 Hz, 1H, H-7); $^{13}C$ NMR ($CDCl_3$, 75.46 MHz): $\delta$156.16, 133.14, 132.55, 124.7, 119.35, 117.97, 103,56, 75.6, 68.48, 49.45, 26.97, 26.61. Analysis calc'd for $C_{12}H_{13}NO_3$: C, 65.71; H, 5.93; N, 6.38; Found: C, 65.82; H, 6.01; N, 6.45.

EXAMPLE 11

Stereoselective esterification of the racemic diol ((±)trans-3,4 -dihydroxy-3,4-dihydro-2,2-dimethyl-2H-1-benzopyran-6-carbonitrile) was carried out with an excess of isopropenyl acetate (0.16M) as the acyl donor, and 4.5 mM diol in toluene (10 mL), in the presence of water (1 mL/L) in 50 mL flasks. The reaction was started by addition of lipase (8 mg/mL). The reaction temperature was 30° C., and agitated at 400 rpm. The progress of the reaction was monitered by chiral HPLC.

Stereoselective esterification of was conducted in toluene, with an excess of isopropenyl acetate (0.32M) as the acylating agent. The title compound was dissolved in toluene (10 g/L, 0.046M), to which isopropenyl acetate was added. To start the reaction, 8 g/L *Candida cylindraceae* lipase from Biocatalyst was added. The reaction temperature was 30° C. and agitated at 450 rpm. During the reaction the optical purity of the diol was monitored by chiral HPLC. 5 The reaction mixture containing the enzyme was filtered using a Whatman 54 filter paper to remove the lipase. The toluene layer (1 L) was extracted with water (2×2L) to remove the title compound from toluene. The water layer was separated, to which SP-207 resin (2% w/v) was added and stirred overnight. The resin was then removed by filtration through a O coarse sintered glass funnel, then washed with water (2×100 mL) and air dried. The dried resin was then washed twice with cyclohexane (100 mL). The washed resin was then extracted with tert-butyl methyl ether (2×100 mL). The organic layer was dried over anhydrous magnesium sulfate, then the solvent removed under reduced pressure to produce a yellow waxy solid. The title compound was further purified by preparative chromatography on reverse phase C-18 column and water:methanol (1: 1) as the mobile phase. The results are shown in Table 10 below. Reactions with lipase PS-30 and *Geotrichum candidum lipase* were carried out under similar conditions and the results are also shown in Table 10.

TABLE 10

| Enzyme | Diol Yield (%) | Diol Optical Purity (%) |
|---|---|---|
| Candida cylindraceae lipase | 45 | 97 |
| Pseudomonas sp. (Amano PS-30) | 40 | 90 |
| Geotrichum candidum lipase | 40 | 87 |

What is claimed is:

1. A process for preparing a chiral epoxide of formula

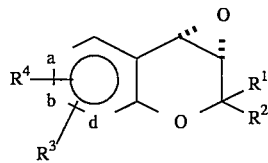

wherein a, b, and d are all carbon atoms or one of a, b and d is a nitrogen atom or —NO— and the others are carbon atoms;

$R^1$ and $R^2$ are independently hydrogen, alkyl or arylalkyl; or $R^1$ and $R^2$ taken together with the carbon atom to which they are attached form a 5- to 7-membered carbocyclic ring;

$R^3$ is hydrogen, alkyl, haloalkyl, alkenyl, alkynyl, cycloalkyl, arylalkyl, cycloalkylalkyl, —CN, —$NO_2$, —COR COOR, —CONHR, —CONRR', — $CF_3$, S—alkyl, —SOalkyl, —$SO_2$alkyl,

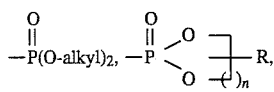

halogen, amino, substituted amino, OH, —O—alkyl, —OCF₃, —OCH₂CF₃, —OCOalkyl, —OCONRalkyl, —NRCOalkyl, —NRCOOalkyl or —NRCONRR' wherein R and R' in each of the above groups is independently hydrogen, alkyl, haloalkyl, aryl, arylalkyl, cycloalkyl, or (cycloalkyl)alkyl;

R⁴ is hydrogen, alkyl, —OH, —O—alkyl, amino, substituted amino, —NHCOR, —CN or —NO₂; and n is an integer of 1 to 3; comprising the step of treating a compound of formula

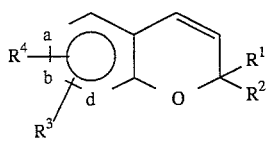

with a microorganism or cell extracts thereof capable of catalyzing the stereoselective epoxidation of compounds of the formula III wherein said microorganism is selected from the group consisting of *Arthrobacter rubellus* (ATCC 21495), *Corynebacterium alkanum* (ATCC 21194), *Corynebacterium* sp. (ATCC 43752), *Cunninghamella echinulata* (ATCC 9244), *Curvularia lunata* (ATCC 12017), *Diplodia gossypina* (ATCC 10936), *Hansenula fabianii* (ATCC 58045), *Hansenula polymorpha* (ATCC 26012), *Helicostylum elegans* (ATCC 12745), *Mortierella ramanniana* (ATCC 38191 and ATCC 24786), *Mucor hiemalis* (ATCC 89778), *Mycobacterium vacca* (ATCC 29678), *Nocardia globerula* (ATCC 21505), *Pseudomonas oleovorans* (ATCC 29347) and *Rhodococcus erythropolis* (ATCC 4277) and effecting said stereoselective epoxidation to provide said compounds of formula I.

2. The process of claim 1, wherein said compound of formula I where a, b and d are carbon atoms; R₁ and R₂ are methyl, R₃ is hydrogen and R₄ is cyano is prepared.

3. A process for preparing compounds having potassium channel activating activity of the formula

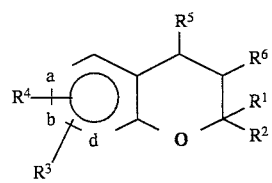

wherein a, b, and d are all carbon atoms or one of a, b and d is a nitrogen atom or —NO— and the others are carbon atoms;

R¹ and R² are independently hydrogen, alkyl or arylalkyl; or R¹ and R² taken together with the carbon atom to which they are attached form a 5- to 7-membered carbocyclic ring;

R³ is hydrogen, alkyl, haloalkyl, alkenyl, alkynyl, cycloalkyl, arylalkyl, cycloalkylalkyl, —CN, —NO₂, —COR, COOR, —CONHR, —CONRR', —CF₃, S—alkyl, —SOalkyl, —SO₂alkyl,

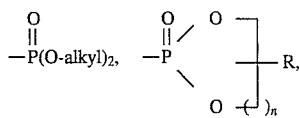

halogen, amino, substituted amino, OH, —O—alkyl, —OCF₃, —OCH₂CF₃, —OCOalkyl, —OCONRalkyl, —NRCOalkyl, —NRCOOalkyl or —NRCONRR' wherein R and R' in each of the above groups is independently hydrogen, alkyl, haloalkyl, aryl, arylalkyl, cycloalkyl, or (cycloalkyl)alkyl;

R⁴ is hydrogen, alkyl, —OH, —O—alkyl, amino, substituted amino, —NHCOR, —CN or —NO₂;

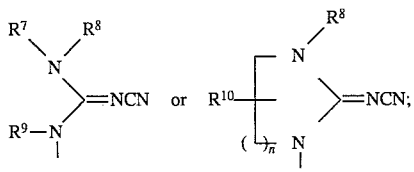

R⁵ is

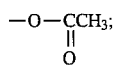

R⁶ is hydrogen, hydroxy or

R⁷ and R⁸ are independently hydrogen, alkyl, alkenyl, aryl, (heterocyclo)alkyl, heterocyclo, arylalkyl, cycloalkyl (cycloalkyl)alkyl or substituted alkyl wherein the substituents include alkoxy, alkylthio and substituted amino; or R₇ and R₈ taken together with the nitrogen atom to which they are attached form 1-pyrrolidinyl, 1-piperidinyl, 1-azepinyl, 4-morpholinyl, 4-thiamorphilinyl, 1-piperazinyl, 4-alkyl-1-piperazinyl or 4-arylalkyl-1-piperazinyl, wherein each of the so-formed groups can be substituted with alkyl, alkoxy, alkylthio, halogen or trifluoromethyl;

R⁹ and R¹⁰ are independently hydrogen, alkyl, alkenyl, aryl, arylalkyl, cycloalkyl or (cycloalkyl)alkyl; or R¹⁰ can be an aryl group fused to 2 carbon atoms of the cyanoguanidine ring portion; and n is an integer of 1 to 3; which comprises the steps of preparing a chiral epoxide of formula

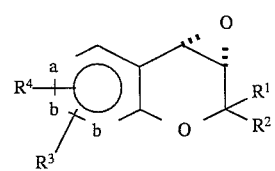

by treating a compound of formula

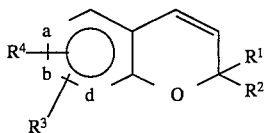

III with a microorganism or cell extracts thereof capable of catalyzing the stereoselective epoxidation of compounds of the formula III wherein said microorganism is selected from the group consisting of *Arthrobacter rubellus* (ATCC 21495), *Corynebacterium alkanum* (ATCC 21194), Corynebacterium sp. (ATCC 43752), *Cunninghamella echinulata* (ATCC 9244), *Curvularia lunata* (ATCC 12017), *Diplodia gossypina* (ATCC 10936), *Hansenula fabianii* (ATCC 58045), *Hansenula polymorpha* (ATCC 26012), *Helicostylum elegans* (ATCC 12745), *Mortierella ramanniana* (ATCC 38191 and ATCC 24786), *Mucor hiemalis* (ATCC 89778), *Mycobacterium vacca* (ATCC 29678), *Nocardia globerula* (ATCC 21505), *Pseudomonas oleovorans* (ATCC 29347) and *Rhodococcus erythropolis* (ATCC 4277) and effecting said stereoselective epoxidation to provide said epoxide of formula I; and converting said epoxide of formula 1 to provide the compounds of formula V.

* * * * *